(12) United States Patent
Liu et al.

(10) Patent No.: US 10,179,802 B2
(45) Date of Patent: *Jan. 15, 2019

(54) CONOTOXIN PEPTIDE κ-CPTX-BTL04, PREPARATION METHOD THEREFOR, AND USES THEREOF

(71) Applicant: BGI SHENZHEN, Guangdong (CN)

(72) Inventors: Jie Liu, Guangdong (CN); Zhilong Lin, Guangdong (CN); Bo Wen, Guangdong (CN); Ting Tong, Guangdong (CN); Fen Mo, Guangdong (CN); Chao Peng, Guangdong (CN); Qiong Shi, Guangdong (CN)

(73) Assignee: BGI SHENZHEN (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/539,752

(22) PCT Filed: Dec. 26, 2014

(86) PCT No.: PCT/CN2014/095198
§ 371 (c)(1),
(2) Date: Jun. 26, 2017

(87) PCT Pub. No.: WO2016/101277
PCT Pub. Date: Jun. 30, 2016

(65) Prior Publication Data
US 2018/0170963 A1    Jun. 21, 2018

(51) Int. Cl.
| | | |
|---|---|---|
| *C07K 7/06* | (2006.01) | |
| *A61K 38/08* | (2006.01) | |
| *A61K 38/00* | (2006.01) | |
| *C07K 1/04* | (2006.01) | |
| *C07K 1/06* | (2006.01) | |
| *C12N 5/10* | (2006.01) | |
| *C12N 15/63* | (2006.01) | |

(52) U.S. Cl.
CPC .............. *C07K 7/06* (2013.01); *A61K 38/08* (2013.01); *C07K 1/04* (2013.01); *C07K 1/06* (2013.01); *C07K 1/061* (2013.01); *C12N 5/10* (2013.01); *C12N 15/63* (2013.01); *A61K 38/00* (2013.01)

(58) Field of Classification Search
None
See application file for complete search history.

(56) References Cited

FOREIGN PATENT DOCUMENTS

| CN | 1237584 A | 9/2011 |
| WO | 9734925 A1 | 9/1997 |
| WO | WO2015022575 | * 2/2015 |

OTHER PUBLICATIONS

Wikipedia "Expression Vector"and "Transformation (genetics)" accessed from wikipedia on May 25, 2018 (Year: 2018).*
Fan, CX et al, "A Novel conotoxin from Conus betulinus, kappa-BtX, unique in cysteine pattern and in function as a specific BK channel modulator." Journal of Biological Chemistry. vol. 278 No. 15. 2003. pp. 1264-12633.
Patent Cooperation Treaty (PCT), International Search Report and Written Opinion for Application PCT/CN2014/095198 filed Dec. 26, 2014, dated Oct. 8, 2015, International Searching Authority, CN.

* cited by examiner

*Primary Examiner* — Adam Weidner
(74) *Attorney, Agent, or Firm* — McDonald Hopkins LLC

(57) ABSTRACT

Provided are a conotoxin peptide κ-CPTx-btl04 and a derivative polypeptide. The amino acid sequence of the conotoxin peptide is indicated by SEQ ID NO: 1. Also provided are a conotoxin peptide preparation method and uses of the conotoxin peptide in the treatment of diseases related to a calcium ion channel.

10 Claims, 2 Drawing Sheets
Specification includes a Sequence Listing.

SEQUENCE LISTING

<160> NUMBER OF SEQ ID NOS: 2

<210> SEQ ID NO 1
<211> LENGTH: 11
<212> TYPE: PRT
<213> ORGANISM: artificial sequence
<220> FEATURE:
<223> OTHER INFORMATION: synthetic peptide

<400> SEQUENCE: 1

Ser Leu Cys Cys Pro Glu Asp Arg Trp Cys Cys
1               5                   10

<210> SEQ ID NO 2
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 2
tccttgtgct gcccagaaga taggtggtgc tgt                    33

CONOTOXIN PEPTIDE κ-CPTX-BTL04, PREPARATION METHOD THEREFOR, AND USES THEREOF

CROSS-REFERENCE TO RELATED APPLICATION

This application is a 35 U.S.C. 371 national stage filing of PCT Application No. PCT/CN2014/095198, filed on Dec. 26, 2014, which is incorporated herein in its entirety by reference.

REFERENCE TO SEQUENCE LISTING SUBMITTED ELECTRONICALLY VIA EFS-WEB

The content of the electronically submitted sequence listing (Name: 99Sequencelisting.txt; Size: 679 bytes; and Date of Creation: Oct. 17, 2017) is herein incorporated by reference in its entirety.

TECHNICAL FIELD

The present invention relates to the field of biomedical technology and, in particular, to a novel conotoxin peptide κ-CPTx-btl04, a polynucleotide encoding the peptide, a construct, an expression vector and a host cell comprising the polynucleotide, natural extraction and synthetic methods of the peptide, and the pharmaceutical use of the peptide.

BACKGROUND ART

Calcium ion channel is a kind of transmembrane protein widely distributed in excitatory cells, which can regulate entry of extracellular $Ca^{2+}$ into the cytoplasm and participate in a series of $Ca^{2+}$-dependent physiological activities such as hormonal and neurotransmitter releases, muscle contraction and cell signaling and so on. According to different sensitivities to voltage, calcium ion channels can be divided into low-voltage activated calcium ion channel (LVA) or T-type calcium channel (Cav3.x) and high-voltage activated calcium ion channel, wherein HVA calcium channel includes L-type (Cav1.x), P/Q-type (Cav2.1), N-type (Cav2.2) and R-Type (Cav2.3) calcium channels. The Cav1.x channel participates in muscle contraction and cell secretion and the Cav2.x participates in neurotransmitter release and neuronal excitatory regulation. The calcium channel consists of α-subunit having the main function and β, γ and δ subunits having the auxiliary function.

Calcium channel blockers are widely found in the venom of animals, such as centipedes, spiders and the like. Many drugs of calcium channel blockers such as dihydropyridine small molecules have been developed. Typical drugs include the selective calcium ion channel blocker nifedipine, which is mainly used in the clinical treatment of hypertension, coronary heart disease, arrhythmia, angina pectoris, cerebrovascular diseases and the like, and belongs to a class of targeted drugs having the most wide and highly frequent application currently.

However, relatively few drugs of polypeptide calcium channel blockers have been currently developed, and as an example, Ziconotide is a class of N-type calcium channel blockers and is useful for the treatment of refractory chronic pain. Polypeptide calcium channel blockers, due to their many advantages, such as high selectivity, high lipophilicity and high safety, will become a hotspot in the future development of drugs of calcium channel blockers.

Hypertension is one of the most common cardiovascular diseases in the world today and is a major risk factor for cardiovascular and cerebrovascular diseases. The research results published by Center for Chronic Disease Prevention and Control of China (CDC) show that the number of hypertensive patients in China has exceeded 330 million, and on average, one in every 3 adults is a hypertensive patient. There are five types of antihypertensive drugs at first-line, namely, calcium channel blockers (CCB), angiotensin converting enzyme inhibitors (ACE I), angiotensin receptor blockers (ARB), diuretics and β-receptor blockers. Among them, calcium channel blockers act as the main force of the retail market of antihypertensive drugs currently, and reduce blood pressure mainly through blocking the calcium channels on myocardium and vascular smooth muscle cell membranes, inhibiting influx of extracellular calcium ions so as to decrease the intracellular calcium ion levels, and thereby lead to the decreased contraction of the cardiovascular and other tissue smooth muscles and vasodilatation, which thereby reduces blood pressure.

*Conus* is a class of toxic animals widely distributed in the tropical marine, and the venom thereof contains a large number of polypeptide ion channel active substances, such as ω-Conotoxin, which can specifically block the voltage-sensitive calcium ion channel, and thus it is an important natural resource for development of antihypertensive drugs of polypeptide calcium channel blockers.

SUMMARY

It is an object of the present invention to provide a novel conotoxin peptide κ-CPTx-btl04, a polynucleotide encoding the peptide, a construct, an expression vector and a transformed host cell comprising the polynucleotide, natural extraction and synthetic methods of the peptide, and the pharmaceutical use of the peptide.

The present invention achieves the above object by the following technical scheme:

In a first aspect, the present invention provides a conotoxin peptide κ-CPTx-btl04, which is:

(a) a polypeptide having the amino acid sequence shown in SEQ ID NO: 1; or (b) a polypeptide derived from polypeptide (a) by substitution, addition and deletion of one or more amino acids in the amino acid sequence of SEQ ID NO: 1 of polypeptide (a) and having the function of polypeptide (a); wherein the amino acids to be substituted, added or deleted do not include cysteine; the function is an activity to inhibit calcium ion channels;

the amino acid sequences of polypeptides (a) and (b) contain two pairs of disulfide bonds, which is required for the polypeptide to play its inhibitory activity on calcium ion channels, so that the cysteine in the amino acid sequence as shown in SEQ ID NO: 1 cannot be substituted, added or deleted.

In the above mentioned conotoxin peptide κ-CPTx-btl04, it is preferred that the substitution of the one or more amino acids is selected from the group consisting of:

(i) substitution of the serine at position 1 with threonine;

(ii) substitution of the leucine at position 2 with isoleucine or valine;

(iii) substitution of the tryptophan at position 9 with tyrosine or phenylalanine.

The inventors of the present invention firstly extracted and identified the conotoxin peptide κ-CPTx-btl04 of the present invention from the venom ducts of *Conus betulinus* native to Hainan, which has the amino acid sequence of SLCCPEDRWCC (i.e., SEQ ID NO: 1), and a molecular weight of 1313.47 daltons.

The inventors also found that the original function of the amino acid sequence shown in SEQ ID NO: 1 can be retained upon a specific substitution of one or more specific amino acid residues in the amino acid sequence shown in SEQ ID NO: 1, i.e., generating the polypeptide (b).

In a second aspect, the present invention provides a polynucleotide encoding the conotoxin peptide κ-CPTx-btl04 as described in the first aspect.

In a specific embodiment, when the conotoxin peptide κ-CPTx-btl04 has an amino acid sequence as shown in SEQ ID NO: 1, the polynucleotide encoding the peptide has a nucleotide sequence as shown in SEQ ID NO: 2, i.e., the nucleotide sequence thereof is: TCCTTGTGCTGCCCA-GAAGATAGGTGGTGCTGT.

In a third aspect, the present invention provides a nucleic acid construct comprising the polynucleotide as described in the second aspect, and one or more control sequences operably linked thereto and being able to direct the production of the polypeptide in an expression host.

In a fourth aspect, the present invention provides an expression vector comprising the nucleic acid construct as described in the third aspect.

In a fifth aspect, the present invention provides a transformed cell into which the nucleic acid construct as described in the third aspect or the expression vector as described in the fourth aspect is transformed.

In a sixth aspect, the present invention provides a use of the conotoxin peptide κ-CPTx-btl04 as described in the first aspect in the manufacture of a medicament for inhibiting a calcium ion channel; preferably, the calcium ion channel is a high-voltage activated calcium ion channel.

The inventors have studied the biological activity of the conotoxin peptide κ-CPTx-btl04 of the present invention. Specifically, the effect of the conotoxin peptide κ-CPTx-btl04 of the present invention on the dorsal root ganglion cells (DRG cells) ion channels is detected by using a whole-cell patch clamp method. In the experiment, two depolarization stimuli are given: the first is at from −90 mV to −30 mV for 250 ms, the second is at from −60 mV to 0 mV for 250 ms, the interval between the two stimuli is 500 ms, and the LVA calcium channel and HVA calcium channel are recorded simultaneously. By comparison analysis with the activity of Nifedipine (the first generation of calcium channel blockers, belonging to antihypertensive, anti-angina pectoris drugs, one of the world's best-selling drugs in the mid-80s of the 20th century) as a positive control, its effect of inhibiting calcium ion channels and its subsequent application are determined.

The inventors of the present invention have found that the conotoxin peptide κ-CPTx-btl04 of the present invention is effective in suppressing the current of the high-voltage activated calcium ion channels (HVA) and the inhibitory effect is higher than that of Nifedipine as a positive control.

In a seventh aspect, the present invention provides a use of the conotoxin peptide κ-CPTx-btl04 as described in the first aspect in the manufacture of a medicament for the treatment of a cardiovascular disease; preferably, the cardiovascular disease is hypertension, angina pectoris or coronary heart disease.

According to the sixth aspect, since the conotoxin peptide κ-CPTx-btl04 of the present invention is effective in suppressing the current of the high-voltage activated calcium ion channels (HVA), it can be used for the treatment of diseases such as hypertension, angina pectoris and coronary heart disease.

In an eighth aspect, the present invention provides a pharmaceutical composition comprising the conotoxin peptide κ-CPTx-btl04 as described in the first aspect and a pharmaceutically acceptable carrier.

In a ninth aspect, the present invention provides a method for producing the conotoxin peptide κ-CPTx-btl04 as described in the first aspect, comprising:

(1) synthesizing the linear peptide of the conotoxin peptide κ-CPTx-btl04 according to its amino acid sequence by solid-phase chemical synthesis, preferably by fluorenyl-methoxycarbonyl solid-phase chemical synthesis;

(2) performing oxidative refolding of the linear peptide obtained in step (1) with glutathione method.

In addition, when the conotoxin peptide κ-CPTx-btl04 is a polypeptide having the amino acid sequence shown in SEQ ID NO: 1, it can also be obtained by extraction from a natural organism. Specifically, the inventors extracted toxin polypeptides from the venom ducts of *Conus betulinus* native to Hainan and then performed the steps of separation and identification to obtain the polypeptide; preferably, strong cation exchange high performance liquid chromatography is used for the separation; preferably, mass spectrometry is used for the identification of polypeptides.

In a specific embodiment, the conotoxin peptide κ-CPTx-btl04 having the amino acid sequence shown in SEQ ID NO: 1 was extracted and identified by the following steps:

Collecting *Conus betulinus* native to Hainan, taking venom ducts and extracting toxin polypeptide therefrom were firstly performed. After reductive alkylation treatment with dithiothreitol (DTT) and iodoacetamide (IAM), the toxin polypeptides were fractionated by using strong cation exchange high performance liquid chromatography (SCX-HPLC) and then detected by using nano-high performance liquid chromatography-mass spectrometry (NanoLC-MS/MS) for mass spectrum of the peptide. The resulting mass spectrometry data was parsed and analyzed bioinformatically to obtain the complete amino acid sequence of the conotoxin polypeptide.

Beneficial Effect

The conotoxin peptide κ-CPTx-btl04 of the invention is available from natural active animal resource, belongs to calcium channel blockers, and has the advantages of high selectivity, high lipophilicity and high safety compared with traditional small molecule medicine. As it has simple structure, is easy to be artificially synthesized, and can effectively inhibit the current of calcium channel and the inhibitory activity is higher than that of Nifedipine, it can be widely used in the treatment of calcium ion channel related diseases; for example, in clinical practice, it has great potential in the treatment of hypertension, heart disease, angina pectoris and other diseases.

DETAILED DESCRIPTION

For the purpose of understanding the present invention, the present invention is exemplified as follows. It will be apparent to those skilled in the art that the examples are merely illustrative of the invention and should not be construed as a specific limitation of the present invention.

Example 1 Extraction and Identification of the Conotoxin Peptide κ-CPTx-Btl04 of the Present Invention 1. Extraction and Reductive Alkylation of *Conus* Venom Four *Conus betulinus* native to Hainan were dissected after smashing their shells, and then the venom ducts thereof were clipped and the *Conus* venoms were collected. Bradford method was performed to determine the protein concentration in the venom, which was 6.48 mg/ml. The total amount of protein was 0.5 mg. DTT at a final concentration of 1 mM was added and reacted at 56° C. for 1 h. After reduction and cooling to room temperature, IAM at a final concentration of 55 mM was added to react in dark room at room temperature for 45 min.

2. Enrichment of Toxin Polypeptides

The conotoxin polypeptides obtained as above were then subjected to Strata-X C18 column to enrich the polypeptides in *Conus* venoms. The enrichment by Strata-X C18 was performed according to the following standard procedure: 1) adding 1 ml of methanol to activate the column; 2) adding 1 ml 0.1% FA to balance the column; 3) loading 1 ml venom sample, washing with buffer (5% ACN+0.1% FA), repeating the wash for 3 times; 4) eluting with 100% ACN, collecting the eluent. The molecular weights of the enriched polypeptides were detected by MALDI-TOF-MS.

3. Sequence Identification of the Conotoxin Polypeptides

240 μg peptide mixture was fractionated by a SCX-HPLC (Shimadzu) system: buffer A: 10 mM $KH_2PO_4$ in 25% ACN, pH 3.5; buffer B: further containing 500 mM potassium chloride on the basis of buffer A; Flow rate: 1 ml/min; elution procedure: 0-40% linear binary gradient of buffer B for 10 minutes, 40-90% of buffer B for 2 minutes, 90% of buffer B for 3 minutes; absorbance detection was performed at 214 nm; as a result, a total of 10 fractions were collected through gradient elution. The collected fractions were demineralized by C18 solid phase extraction column (Strata-X, Phenomenex) and then reconstituted with 30 μl of 0.1% formic acid for nanoLC-MS/MS analysis.

4. NanoLC-MS/MS Analysis

LC/MS was from Shimadzu's nano HPLC chromatograph system and AB Sciex's Triple TOF 5600 mass spectrometer system. Each pre-separated polypeptide component was separated by a self-made Ultimate capillary analysis column which had a length of 12 cm, an inner diameter of 75 μm and was filled with Welch Materials brand XB-C18 column material with a particle size of 3 μm and a pore diameter of 120 μm at a flow rate of 300 nl/min. The injection volume for detection was 25 μl and the concentration of Buffer B was evenly increased from 5% to 45% for 40 min for a gradient elution. For mass spectrum acquisition, the electrospray voltage was 2.5 kV, the auxiliary air pressure was 30 PSI, the sheath gas pressure was 15 PSI, and the source temperature was 150° C. The first-order mass spectrum was acquired using a high-resolution mode greater than or equal to 30000. The valence state of parent ions in the range of 2 charges to 5 charges was selected for acquisition of the second-order mass spectrum. After one scanning of the first-order mass spectrum, 30 second-order mass spectrometric fragmentations can be conducted continuously, so that 30 scannings of the second-order spectrum daughter ions can be completed in 250 ms, and more than 120 sheets of the second-order spectrums can be generated per second. The total cycle time was 3.3 seconds.

In the obtained mass spectrometry raw data, the sequence search and alignment result of the mass spectrum corresponding to the conotoxin peptide κ-CPTx-btl04 of the present invention was shown in FIG. 1.

5. Data Analysis

The mass spectrometry raw data obtained by nanoLC-MS/MS detection was format converted into MGF, which then was subjected to data search and identification by Mascot search software. In the obtained polypeptide sequences, the κ-CPTx-btl04 polypeptide having a full length amino acid sequence of SLCCPEDRWCC was selected by sequence feature analysis.

Example 2 Chemical Synthesis of the Conotoxin Peptide κ-CPTx-Btl04 of the Present Invention The conotoxin linear peptide as shown in SEQ ID NO: 1 was synthesized by fluorenylmethoxycarbonyl (Fmoc) solid phase chemical synthesis (customized by GL Biochem (Shanghai) Ltd.).

The chemically synthesized polypeptide was refolded by using glutathione oxidative refolding, i.e.:

The polypeptide was dissolved in a solution at pH 7.4 containing 0.1 M Tris-HCl, 0.1 M NaCl, 5 mM GSH and 0.5 mM GSSG at a mass to volume ratio of 1:10 and reacted at 25° C. for 24 to 48 h. The refolding effect was detected by MALDI-TOF-MS.

Example 3 Inhibitory Activity of the Conotoxin Peptide κ-CPTx-Btl04 of the Present Invention on Calcium Ion Channels The inhibitory activity of the conotoxin peptide κ-CPTx-btl04 of the present invention on calcium ion channels was detected by patch-clamp technique. Specifically, the conotoxin peptide κ-CPTx-btl04 as prepared and refolded in Example 2 was weighed and detected for its effect on rat dorsal root ganglion (DRG) cell ion channels by whole-cell patch-clamp method. Nifedipine was used as a positive control.

Intracellular fluid and extracellular fluid in patch-clamp method were configured as follows:

Extracellular fluid: 140 mM NaCl, 4 mM KCl, 1 mM $MgCl_2$, 2 mM $CaCl_2$, 5 mM D-Glucose monohydrate, 10 mM HEPES (pH=7.4); intracellular fluid: 20 mM KCl, 110 mM potassium aspartate (KAspartic), 1 mM $MgCl_2$, 5 mM EGTA, 10 mM HEPES (pH=7.2).

DRG cells (dorsal root ganglion cells immediately separated from SD rats and cultured) in the thermostatic incubator were taken out, and the culture medium in the culture dish was replaced with a well-balanced extracellular fluid at room temperature to prevent drastic changes in the temperature of the solution. The extracellular fluid was gently added with a pipette along the wall of the dish to prevent the cells shedding from the bottom of the dish. The cells in the extracellular fluid were placed under an inverted microscope for observation, and those cells with smooth cell membrane and homogeneous cytoplasm were selected, and subjected to the patch clamp test at a room temperature of 20-25° C.

100 μl borosilicate glass blank was used as glass microelectrode material. A two-step drawing was performed by a drawing instrument to make the diameter of the electrode tip be about 1.5-3.0 μm, and the initial resistance of the glass microelectrode upon immersion into a liquid be 2-4 MΩ. The electrode was filled and installed followed by being moved below the liquid surface, and then a continuous positive pressure was immediately applied to ensure that the electrode tip was clean, that is, conducting liquid junction potential compensation. Under the inverted microscope, a microelectrode was moved over the selected cell and close to the cell, the positive pressure was removed and a slight negative pressure was applied for attraction. After forming a high impedance Giga-Ohm (GΩ) seal between the electrode and the cell membrane, an electrode fast capacitance compensation was conducted immediately. The cell was then clamped at −60 mV, and a short and strong negative pressure was applied, thereby breaking the cell membrane clamped in the microelectrode rapidly and then performing cell low capacitance compensation. After forming the whole cell recording pattern, the cell was clamped at −90 mV for 4-6 min, and then the cell was subjected to two depolarization stimuli: the first one was at from −90 mV to −30 mV, for 250 ms, and the second one was at from −60 mV to 0 mV, for 250 ms, the interval between the two stimuli was 500 ms, and the LVA calcium channel and the HVA calcium channel were recorded at the same time. A polypeptide sample was added to the extracellular fluid to give an effective concentration of 10 μM. The changes in the recorded calcium channel current were observed simultaneously (the experiment was repeated three times and the result was an average of three replicates). The series resistance (Rs) was always constant within the range of <10 MΩ during the experiment, and the system series resistance compensation (Rseries compensation) was between 30 and 70%.

Figure 1:
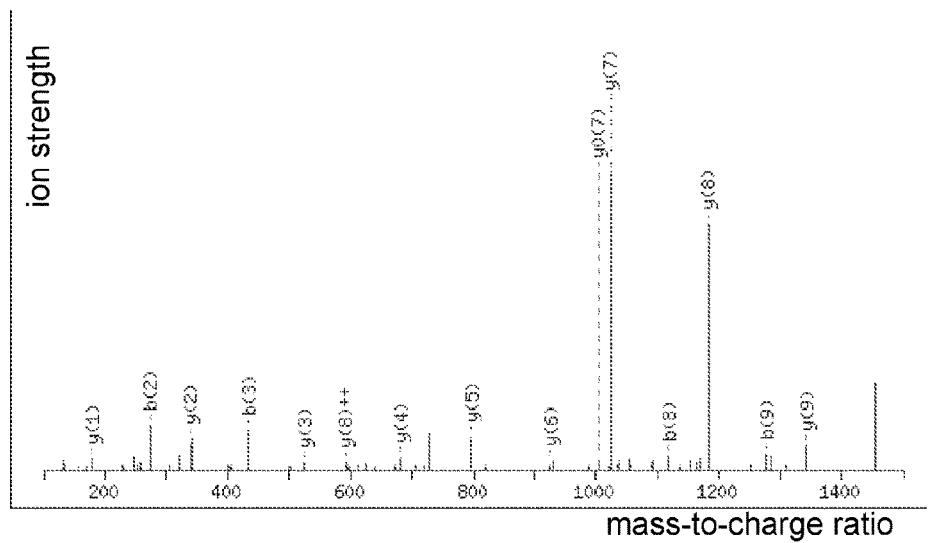
FIG. 1 shows the mass spectrometric identification result of the sequence of the conotoxin peptide κ-CPTx-btl04 of the present invention.
Figure 2:
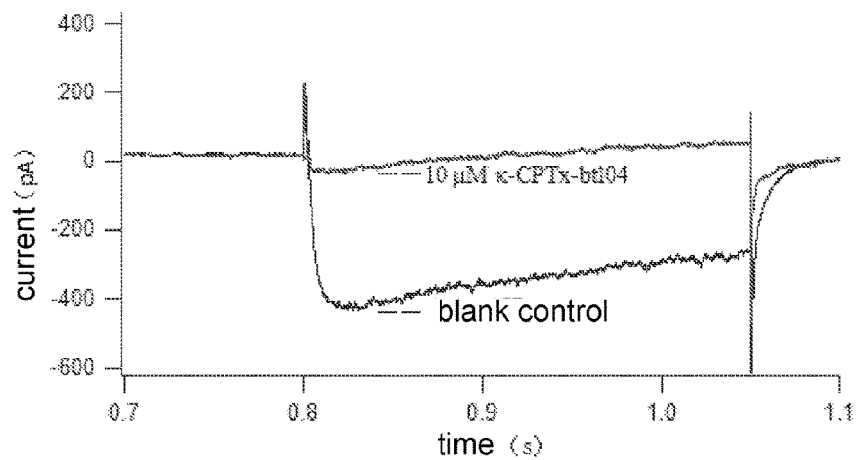
FIG. 2 shows the inhibitory effect of 10 μM conotoxin peptide κ-CPTx-btl04 on high-voltage activated calcium channels.
Figure 3:
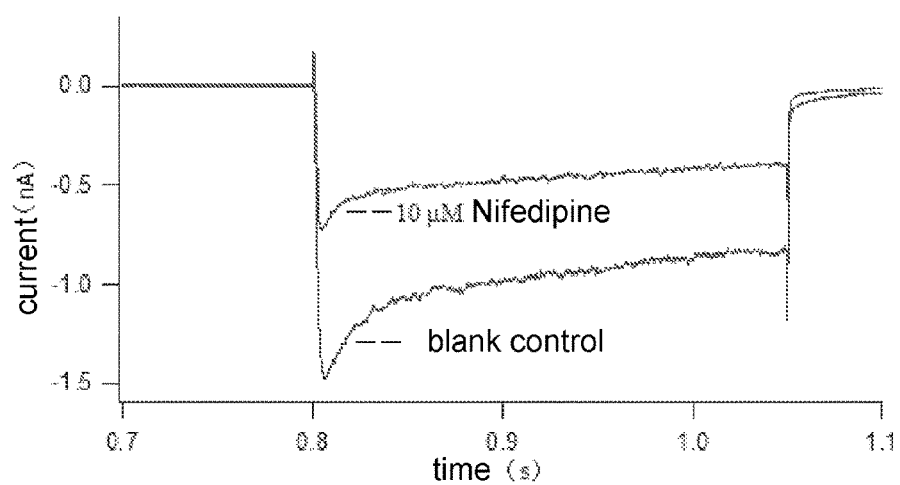
FIG. 3 shows the inhibitory effect of 10 μM Nifedipine on high-voltage activated calcium channels.

The detection results of the conotoxin peptide κ-CPTx-btl04 and Nifedipine were shown in FIG. 2 and FIG. 3 respectively, and the inhibition rate of 10 μM of κ-CPTx-btl04 on HVA calcium channel currents in DRG neuronal cells was 81.18% (as shown in Table 1). The results showed that κ-CPTx-btl04 had a higher inhibition rate on HVA calcium channel currents than Nifedipine at the same concentration, suggesting that it can be used as a candidate drug for antihypertensive drugs.

TABLE 1

Patch clamp detection results of the inhibitory rate of the conotoxin peptide κ-CPTx-btl04 on calcium ion channel

| tested drugs | cell number | current before loading (pA) | current after loading (pA) | inhibition rate (%) |
| --- | --- | --- | --- | --- |
| κ-CPTx-btl04 | 140903009 | −438.34 | −82.49 | 81.18 |
| Nifedipine | 140904007 | −1471.35 | −734.31 | 50.09 |

The applicant states that the present invention illustrates the product, the detailed preparation process and the use thereof by the above examples, however, the present invention is not limited to the above-described detailed preparation process and use, and it is not meant that the present invention has to be carried out with respect to the above-described detailed manufacturing process and use described above. It will be apparent to those skilled in the art that any improvements to the present invention, equivalents of the raw materials of the present invention, addition of auxiliary ingredients, selection of specific means, etc., all fall within the protection scope and disclosure scope of the present invention.

The invention claimed is:

1. A purified conotoxin peptide κ-CPTx-btlo4, which is derived from a polypeptide having the amino acid sequence of SEQ ID NO:1 by substitution of one or more amino acids therein, wherein the substitution of the one or more amino acids is selected from the group consisting of:
   (i) substitution of the serine at position 1 with threonine;
   (ii) substitution of the leucine at position 2 with isoleucine or valine; and
   (iii) substitution of the tryptophan at position 9 with tyrosine or phenylalanine.

2. A polynucleotide encoding the conotoxin peptide κ-CPTx-btlo$_4$ according to claim 1.

3. A nucleic acid construct comprising the polynucleotide of claim 2, and one or more control sequences operably linked thereto and being able to direct the production of the polypeptide in an expression host.

4. An expression vector comprising the nucleic acid construct of claim 3.

5. A transformed cell into which the nucleic acid construct of claim 3 is transformed.

6. A method for inhibiting a calcium ion channel comprising administration of the conotoxin peptide κ-CPTx-btlo$_4$ according to claim 1.

7. A method for producing the conotoxin peptide κ-CPTx-btlo$_4$ according to claim 1, which comprises:
   (1) synthesizing the linear peptide of the conotoxin peptide κ-CPTx-btlo$_4$ according to its amino acid sequence by solid-phase chemical synthesis;
   (2) performing oxidative refolding of the linear peptide obtained in step (1) with glutathione method.

8. The method according to claim 7, wherein the solid-phase chemical synthesis is fluorenylmethoxycarbonyl solid-phase chemical synthesis.

9. A transformed cell into which the expression vector of claim 4 is transformed.

10. The method according to claim 6, wherein the calcium ion channel is a high-voltage activated calcium ion channel.

\* \* \* \* \*